United States Patent [19]
Tower

[11] Patent Number: 5,695,498
[45] Date of Patent: Dec. 9, 1997

[54] STENT IMPLANTATION SYSTEM

[75] Inventor: Allen J. Tower, North Lawrence, N.Y.

[73] Assignee: Numed, Inc., Nicholville, N.Y.

[21] Appl. No.: 608,123

[22] Filed: Feb. 28, 1996

[51] Int. Cl.$^6$ .................................................. A61F 11/00
[52] U.S. Cl. .................... 606/108; 606/198; 606/194; 606/195
[58] Field of Search .................... 606/108, 194, 606/195; 604/96, 198

[56] References Cited

U.S. PATENT DOCUMENTS

| | | | |
|---|---|---|---|
| 4,733,665 | 3/1988 | Palmaz | 606/108 |
| 4,739,762 | 4/1988 | Palmaz . | |
| 4,776,337 | 10/1988 | Palmaz . | |
| 4,793,348 | 12/1988 | Palmaz . | |
| 4,793,350 | 12/1988 | Mar et al. | 606/195 |
| 4,819,751 | 4/1989 | Shimada et al. | 606/194 |
| 5,161,547 | 11/1992 | Tower . | |
| 5,217,483 | 6/1993 | Tower . | |
| 5,275,622 | 1/1994 | Lazarus et al. | 606/194 |
| 5,352,199 | 10/1994 | Tower | 604/96 |

FOREIGN PATENT DOCUMENTS

| | | | |
|---|---|---|---|
| 9112847 | 9/1991 | WIPO | 606/194 |

*Primary Examiner*—Sam Rimell
*Assistant Examiner*—Justine R. Yu
*Attorney, Agent, or Firm*—Harris Beach & Wilcox, LLP

[57] ABSTRACT

A device for implanting a radially expandable stent that includes a balloon catheter having a balloon formed of a material having a memory so that when inflated to a first pressure the two end sections of the balloon expand to a first diameter as the waist therebetween expands to a lesser diameter. The stent is mounted over the waist section of the balloon and is thus locked between the two end sections during initial inflation to the first pressure. Once locked in place, the pressure inside the balloon is raised to a second higher level whereby the entire balloon expands to a larger diameter thus radially expanding the stent.

9 Claims, 1 Drawing Sheet

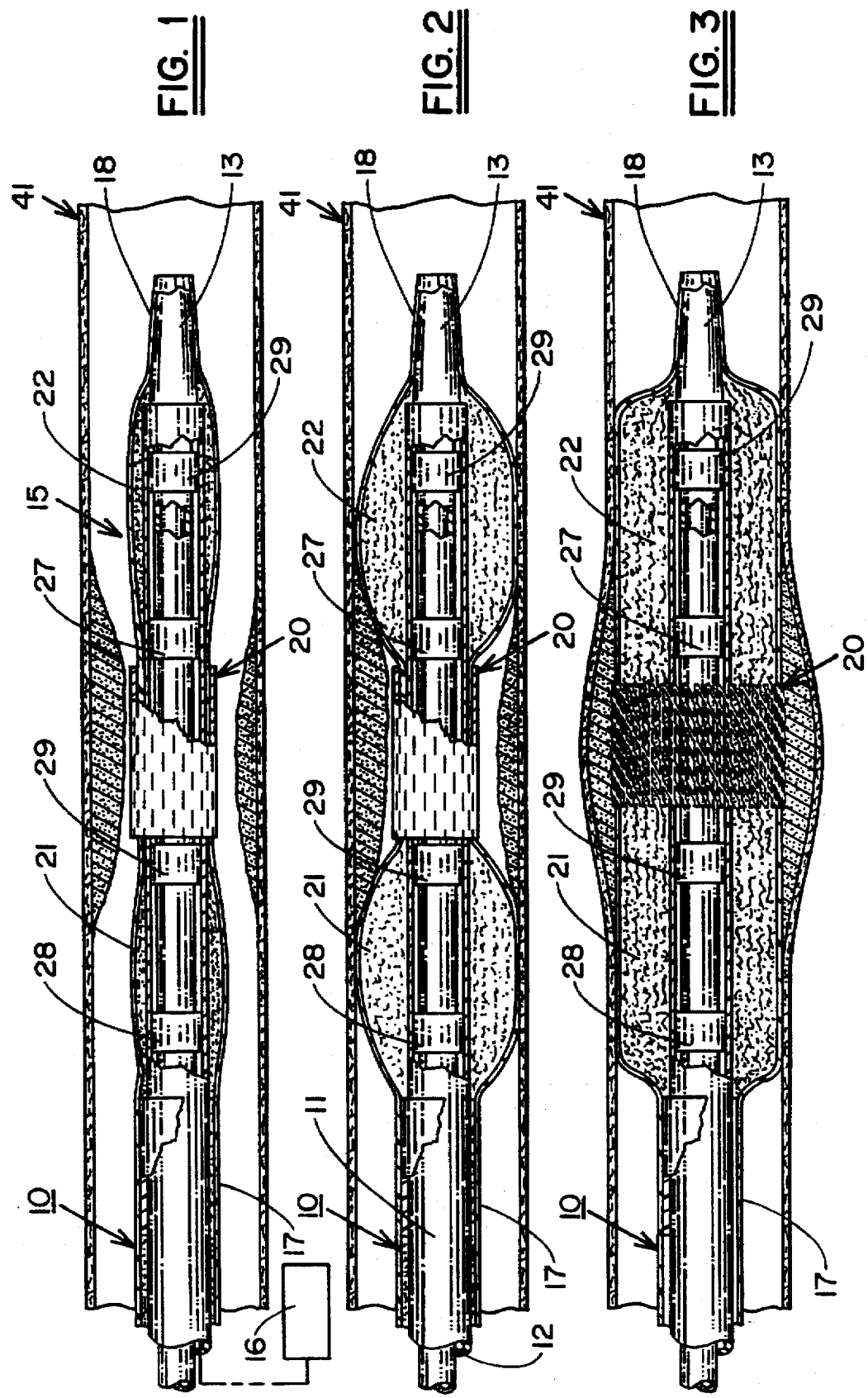

STENT IMPLANTATION SYSTEM

BACKGROUND OF THE INVENTION

This invention relates to a device for implanting an expandable stent and, in particular, to a device for accurately positioning a stent within a body vessel and expanding the stent radially without axial movement of the stent within the vessel.

The basic concept of implantable stents for use in medical applications has been known for a number of years. One primary means of delivering an unexpanded stent into a body vessel or cavity is by use of a balloon catheter. In practice, the stent is mounted at the distal end of the catheter over an inflatable membrane (balloon) and is carried to a remote treatment area by guiding the catheter through an appropriate body vessel. An image band made of a noble metal such as platinum is typically mounted at the distal end of the catheter which permits the catheter to be easily tracked and positioned radiographically by a fluoroscopic or other suitable means. Once it is determined that the stent is properly positioned, the balloon is inflated thereby forcing the stent outwardly into a fully expanded position.

It has been found, however, that some balloons can inflate non-uniformly and thus shift the stent axially leading to improper implantation of the stent. Oftentimes, the attending physician is unaware of any misalignment because the single image band does not move during the implantation process or give any other indication of improper positioning. In extreme cases, the stent is pushed completely off the distal end of the catheter by the balloon whereupon the stent must be retrieved surgically. This places the patient at additional risk and can cause unwanted discomfort.

Stents that are fabricated of non-maluable materials such as stainless steel are more susceptible to axial misalignment than more flexible or malleable stents. Although the reason for this is not fully understood at this time, it is believed that stents formed of the stiffer materials cannot conform readily to a non-uniformly inflated balloon and instead of expanding outwardly are forced axially by the non-uniform pressure being exerted thereon.

SUMMARY OF THE INVENTION

It is therefore a primary object of the present invention to improve devices for implanting radially expandable stents.

It is a further object of the present invention to more accurately position an expandable stent during the implantation process.

It is a still further object of the present invention to prevent axial shifting of a radially expandable stent as it is being implanted within a body cavity.

Another object of the present invention is to prevent the loss of an expandable stent from the insertion device during the implantation procedure.

Yet another object of the present invention is to better facilitate accurate implantation of a stainless steel stent.

A still further object of the present invention is to reduce patient discomfort during the implantation of an expandable stent by quickly and accurately locating the stent within the treatment region and radially implanting the accurately located stent without axial movement thereof.

These and other objects of the present invention are attained by means of a device for implanting a radially expandable stent in a body cavity or body vessel that includes an elongated catheter having a lumen therein for conducting a fluid from the proximal end of the catheter to the distal end. A transaxially expandable balloon is attached to the distal end of the catheter and is placed in fluid flow communication with the lumen whereby the balloon can be inflated with fluid. The balloon is formed of a thin membrane such as a modified polyethylene terephalate copolymer that has a memory so that the two end sections of the balloon are inflated to a given size (diameter) and the waist section to a smaller diameter at a first inflation pressure. Inflating the balloon to a second greater pressure causes the entire balloon to inflate to a larger diameter. An expandable stent is mounted between the two end sections of the balloon over the waist section. As the balloon is being inflated, the stent is first captured between the end sections to prevent axial displacement thereof and is then expanded radially as the balloon is inflated to a larger diameter.

BRIEF DESCRIPTION OF THE DRAWING

For a better understanding of these and other objects of the present invention, reference will be made to the following detailed description of the invention which is to be read in conjunction with the accompanying drawings, wherein:

FIG. 1 is a partial side elevation in section of a body vessel illustrating a balloon catheter embodying the teachings of the present invention contained therein;

FIG. 2 is a side elevation similar to that of FIG. 1 further illustrating the balloon of the catheter inflated to a first pressure wherein a stent is mounted over the balloon is captured between the two end sections of the balloon; and FIG. 3 is a further side elevation of the body vessel showing the balloon inflated to a higher pressure wherein the stent is expanded radially by the balloon into operative contact with the inner wall of the vessel.

DETAILED DESCRIPTION OF THE INVENTION

The present invention will be described with specific reference to a stainless steel stent having a design that is well known and widely used within the industry. Basically the stent is a thin cylindrical member, which when in an unexpandable state, as shown in FIG. 1, has a series of longitudinal slots 31 cut through its wall. The slots are strategically located about the body of the cylinder so that the stent 20 is able to expand radially where a predetermined internal force is applied thereto. The internal force is provided by an inflatable balloon over which the stent is mounted. The delivery vehicle for the stent is typically a balloon catheter.

Although the present invention is ideally suited for implanting a stainless steel stent within a body cavity, it is equally well adapted to implant any type of stent formed of a non-maluable material. The term non-maluable as herein used refers to a material that has a stiffness such that the stent will not conform its shape to that of the balloon in the event the balloon inflates non-uniformly inside the stent. In response to a nonuniform expansion of the balloon, the stent, rather than expanding, will generally move axially toward a region of lower pressure. As noted above, this will cause misalignment of the stent in the body cavity and in extreme cases can drive the stent off the distal end of the catheter.

Turning now to FIG. 1, there is shown a balloon catheter, which is generally referenced 10, being guided into a blood vessel 41. The catheter has an outer hollow shaft 11 containing a lumen 12 through which an inner hollow shaft 13 passes. The inner shaft extends outwardly beyond the distal end of the outer shaft and further contains a smaller lumen (not shown) through which access to a remote body region is gained. Typically, a guide wire (not shown) is passed through the central lumen into the body vessel along which the catheter is guided into a desired region. An axially extended balloon 15 is bonded to the distal end of the outer shaft at point 17 and to the distal end of the inner shaft at point 18. Accordingly, fluid under pressure is delivered from an inflation unit 16 beneath the balloon via lumen 12 thereby causing the balloon to inflate and expand radially. When in an uninflated state, the balloon 15 lies flaccidly against the surface of the inner shaft 13. A stent 20 which is to be implanted is mounted upon the extended end of the inner shaft over the balloon. A slight clamping pressure is applied by the stent against the inner shaft at one or more points to ensure that the stent does not become misaligned or dislodged during insertion. In practice, the axial length of the balloon 15 is about three times that of the stent and the stent is centrally located upon the balloon in assembly.

As disclosed in U.S. Pat. No. 5,352,199 which issued in the name of the present inventor, balloons formed of a thin wall membrane such as modified polyethylene terephalate copolymers can be processed so that the balloon will possess a memory, and thus assume a desired shape when inflated to a predetermined pressure. The membrane is initially heated while it is being inflated using known blow molding technique so that the balloon 15 will attain a desired configuration at the predetermined pressure. This shape is memorized after the membrane has cooled and the balloon deflated. The copolymer has the property that it will reach the desired shape or configuration when inflated to a predetermined pressure. Further inflation of the balloon 15 to a second higher pressure will cause the entire balloon to round out into a cylinder having a larger diameter.

As shown in FIG. 2, the balloon is provided with a memory such that two end sections 21 and 22 of the balloon will expand radially when inflated to a first pressure while a center waist section 33 balloon located under the stent expands radially to a much lesser extent. In practice, each section 21, 22, 33 of the balloon 15 has a transaxial length that is approximately one third of the total axial length of the balloon. Preferably, the end sections 21, 22 will inflate at a pressure of about 40 lbs/in$^2$, and the entire balloon will inflate at a pressure of about 60 lbs/in.

A pair of axially separated image bands 26 and 27 are mounted upon the inner shaft 13 under the balloon 15 to mark the axially disposed outer ends of the stent which are coextensive with the inner ends of the two balloon sections 21, 22. A second pair of image bands 28 and 29 are spaced apart axially from the other two bands and mark the outer ends of the balloon end section 21, 22. The band 26, 27, 28, 29 are formed of a material that is radiographically responsive and thus able to be clearly seen under a fluoroscope or the like. As illustrated in the drawings, the stent carried on the distal end of the catheter is shown being positioned beneath an area of plaque 40 which is obstructing the flow of blood through the blood vessel 41. Use of four image bands 26, 27, 28, 29, in the alignment shown allows the attending physician to accurately determine the exact location of the balloon and the stent mounted within a body cavity.

Once the stent 20 is properly positioned in the treatment region, a fluid under a first pressure is delivered from inflation unit 16 via the outer lumen 12 beneath the balloon. Accordingly, as illustrated in FIG. 2, the two end sections 21, 22 of the balloon inflate to a given diameter to either side of the stent capturing the stent therebetween and preventing the stent from moving axially.

With the stent locked in place against axial movement, the pressure in the balloon 15 is raised to a second higher pressure at which time the balloon rounds out to an elongated configuration as shown in FIG. 3. This rounding out of the balloon forces the stent outwardly in a radial direction into contact with the plaque formation encompassing the inner wall of the blood vessel 41. This, in turn, expands the occluded region and more fully opens the blood vessel. The balloon 15 is now deflated leaving the stent implanted, and the catheter removed from the blood vessel.

Although the present invention has been described with particular reference to implanting a stainless steel stent within an obstructed blood vessel, it should be obvious to one skilled in the art that the invention has broader applications and can be employed to implant any type of radially expandable stent in any number of medical procedures.

While the present invention has been particularly shown and described with reference to the preferred mode as illustrated in the drawing, it will be understood by one skilled in the art that various changes in detail may be effected therein without departing from the spirit and scope of the invention as defined by the claims.

We claim:

1. Apparatus for implanting a radially expandable stent comprising:

a catheter having a longitudinal axis and a lumen for conducting a fluid therethrough;

an axially disposed transaxially expandable balloon attached to said catheter in fluid flow communication with said lumen for inflation of said balloon, said balloon having two end sections and a waist section therebetween;

said balloon being formed of a shape memory material having memory so that two axially separated end sections of the balloon are expanded to a first diameter while the waist section, located between the two end sections, is inflated to a smaller diameter when the balloon is inflated to a first pressure and all sections of the balloon being expanded to a larger diameter when the balloon is inflated to a second higher pressure;

a radially expandable stent mounted in an unexpanded state over the waist section of said balloon between said end sections; and inflation means connected to said lumen for inflating the balloon made from the shape memory material to said first pressure to capture the stent between the two expanded end sections of the balloon to prevent axial movement thereof prior to inflating said balloon to said second higher pressure to inflate the balloon to the larger diameter wherein the stent is expanded radially.

2. The apparatus of claim 1, including image bands mounted upon the catheter within the balloon that are capable of producing radiographic images for accurately locating the stent within a body vessel.

3. The apparatus of claim 2, wherein said image bands includes at least one image band which is disposed axially on either side of the attached stent.

4. The apparatus of claim 3, wherein at least one image band is located adjacent an outer edge of each end section.

5. The apparatus of claim 1 wherein the balloon comprises a thin wall membrane of a modified polyethylene terephalate copolymer.

6. The apparatus of claim 5 wherein said stent is formed of stainless steel.

7. The apparatus of claim 1 wherein said first inflation pressure is about 40 lb/in.$^2$ and said second inflation pressure is about 60 lb/in.$^2$.

8. The apparatus of claim 1, wherein said radially expandable stent is made from a malleable material.

9. The apparatus of claim 1, wherein said radially expandable stent is made from a non-malleable material.

* * * * *